United States Patent
Ozawa (10) Patent No.: US 7,860,329 B2
(45) Date of Patent: Dec. 28, 2010

(54) EDGE ENHANCEMENT PROCESSING UNIT, ENDOSCOPE PROCESSOR, AND COMPUTER PROGRAM PRODUCT

(75) Inventor: Ryo Ozawa, Saitama (JP)

(73) Assignee: Hoya Corporation, Tokyo (JP)

( * ) Notice: Subject to any disclaimer, the term of this patent is extended or adjusted under 35 U.S.C. 154(b) by 1086 days.

(21) Appl. No.: 11/464,623

(22) Filed: Aug. 15, 2006

(65) Prior Publication Data

US 2007/0041655 A1    Feb. 22, 2007

(30) Foreign Application Priority Data

Aug. 17, 2005    (JP)    ............................ P2005-236708

(51) Int. Cl.
    *G06K 9/40*    (2006.01)
(52) U.S. Cl. ........................ 382/254; 382/274; 382/275; 358/3.26; 358/3.27
(58) Field of Classification Search ................ 382/260, 382/274, 275; 358/3.26, 3.27, 463
    See application file for complete search history.

(56) References Cited

U.S. PATENT DOCUMENTS

| | | | | |
|---|---|---|---|---|
| 5,473,384 | A * | 12/1995 | Jayant et al. | ................. 348/470 |
| 5,732,160 | A | 3/1998 | Katoh | |
| 5,923,775 | A * | 7/1999 | Snyder et al. | ................. 382/172 |
| 6,442,203 | B1 * | 8/2002 | Demos | ................. 375/240.16 |
| 6,462,768 | B1 * | 10/2002 | Oakley | ......................... 348/31 |
| 6,741,753 | B1 * | 5/2004 | Moroney | .................... 382/274 |
| 6,900,829 | B1 | 5/2005 | Ozawa et al. | |
| 6,967,673 | B2 | 11/2005 | Ozawa et al. | |
| 7,050,086 | B2 | 5/2006 | Ozawa | |
| 7,298,927 | B2 * | 11/2007 | Nako et al. | ................. 382/298 |
| 2005/0265622 | A1 | 12/2005 | Tokuyama et al. | |

FOREIGN PATENT DOCUMENTS

| | | |
|---|---|---|
| JP | 6-315098 | 11/1994 |
| JP | 8-181889 | 7/1996 |
| JP | 8-206062 | 8/1996 |
| JP | 8-298602 | 11/1996 |
| JP | 9-065173 | 3/1997 |
| JP | 9-154808 | 6/1997 |
| JP | 2001-103340 | 4/2001 |

(Continued)

OTHER PUBLICATIONS

English language Abstract of JP 8-206062, 1995.

(Continued)

*Primary Examiner*—Yosef Kassa
(74) *Attorney, Agent, or Firm*—Greenblum & Bernstein, P.L.C.

(57) ABSTRACT

An edge enhancement processing unit comprising a determination block and a signal processing block is provided. The determination block determines whether the luminance of a surrounding pixel is greater than at zero level. The surrounding pixel is located around a focused pixel. The signal processing block carries out an edge enhancement process for a pixel signal generated by the focused pixel. The edge enhancement process is carried out if the determination block determines that the luminance of the surrounding pixel is greater than at zero level.

20 Claims, 8 Drawing Sheets

FOREIGN PATENT DOCUMENTS

| | | |
|---|---|---|
| JP | 2001-285673 | 10/2001 |
| JP | 2002-143079 | 5/2002 |
| JP | 2002-369794 | 12/2002 |
| JP | 2003-010109 | 1/2003 |
| JP | 2004-032137 | 1/2004 |
| JP | 2004-046329 | 2/2004 |
| JP | 2004-128934 | 4/2004 |
| JP | 2004-260421 | 9/2004 |
| JP | 2005-341021 | 12/2005 |

OTHER PUBLICATIONS

English language Abstract of JP 9-154808, 1997.
English language Abstract of JP 2001-285673, 2001.
English language Abstract of JP 2002-369794, 2002.
English language Abstract of JP 2002-143079, 2002.
English language Abstract of JP 2004-032137, 2004.
English language Abstract of JP 2004-046329, 2004.

* cited by examiner

EDGE ENHANCEMENT PROCESSING UNIT, ENDOSCOPE PROCESSOR, AND COMPUTER PROGRAM PRODUCT

BACKGROUND OF THE INVENTION

1. Field of the Invention

The present invention relates to an edge enhancement process unit that carries out an edge enhancement process for an image signal generated by an imaging device.

2. Description of the Related Art

An edge enhancement process is carried out for an image signal generated by an imaging device comprised in an electric endoscope. The edge enhancement process is ordinarily carried out by calculating the remainder of a signal intensity of luminance signal or color difference signal for a focused pixel and surrounding pixels around the focused pixel, and by adding the remainder to the signal intensity for the focused pixel.

Incidentally, a wide-angle lens may be used for an imaging device, such as an imaging device comprised in an electric endoscope. Such a wide-angle lens distorts an optical image in the side. Such a distorted image is hidden by being colored with black.

Figure 8:
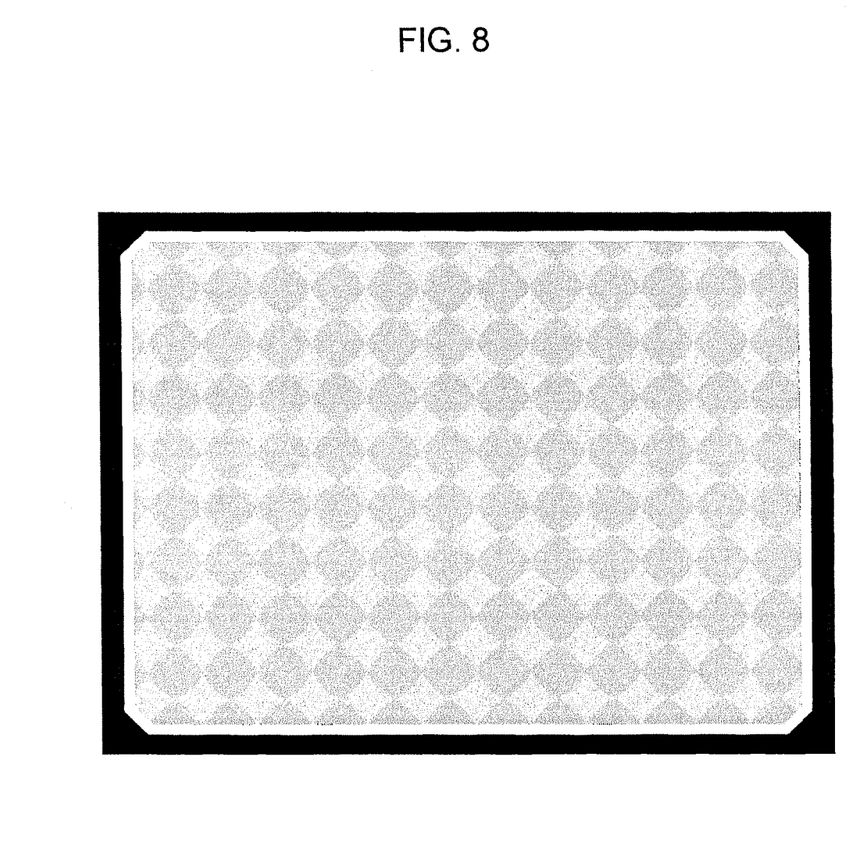
FIG. 8 is an image displayed on a monitor when the edge enhancement process for a pixel neighboring a masked area is not stopped.

When the above-described edge enhancement process is carried out for a pixel neighboring the black-colored pixel, a white line is displayed along the black colored area (see FIG. 8), or an artificial image is displayed. Such a white line or an artificial image is unsightly for a user.

SUMMARY OF THE INVENTION

Therefore, an object of the present invention is to provide an edge enhancement process unit that carries out an edge enhancement process excluding a pixel neighboring the black colored pixel.

According to the present invention, an edge enhancement process unit comprising a determination block and a signal process block is provided. The determination block determines whether the luminance of a surrounding pixel is greater than at zero level. The surrounding pixel is located around a focused pixel. The signal process block carries out an edge enhancement process for a pixel signal generated by the focused pixel. The edge enhancement block is carried out if the determination block determines that the luminance of the surrounding pixel is greater than at zero level.

Further, the signal process block comprises an input terminal, first and second pixel delay circuits, first fourth multiplier circuits, and first and second adder circuits. The input terminal receives a pixel signal generated by a pixel. The first and the second pixel delay circuits are connected to the input terminal sequentially. The first and second multiplier circuits are connected to each output terminal of the first and second pixel delay circuits, respectively. The first multiplier circuit multiplies the pixel signal sent from the first pixel delay circuit. The pixel signal, which is sent from the first pixel delay circuit, is multiplied by a first coefficient. The second multiplier circuit multiplies the pixel signal sent from the second pixel delay circuit. The pixel signal that is sent from the second pixel delay circuit is multiplied by a second coefficient. The third multiplier circuit is connected to the input terminal. The third multiplier circuit multiplies the pixel signal, sent from the input terminal, by a third coefficient. The first adder circuit sums pixel signals output from the first, second, and third multiplier circuits. The fourth multiplier circuit multiplies the pixel signal output from the first adder circuit by zero if the determination block determines that the luminance of the surrounding pixel is at zero level. Alternatively, the fourth multiplier multiplies the pixel signal output from the first adder circuit by a fourth coefficient if the determination block determines that the luminance of the surrounding pixel is at greater than zero level. The second adder circuit adds the pixel signal output from the fourth multiplier circuit to the pixel signal output from the first pixel delay circuit.

Further, the determination block determines whether the luminance of the surrounding pixel is at greater than zero level by determining whether the signal intensity of the color signal component of the pixel signal corresponding to the surrounding pixel is at greater than zero level.

BRIEF DESCRIPTION OF THE DRAWINGS

The objects and advantages of the present invention will be better understood from the following description, with reference to the accompanying drawings in which.

DESCRIPTION OF THE PREFERRED EMBODIMENTS

The present invention is described below with reference to the embodiment shown in the drawings.

Figure 1:
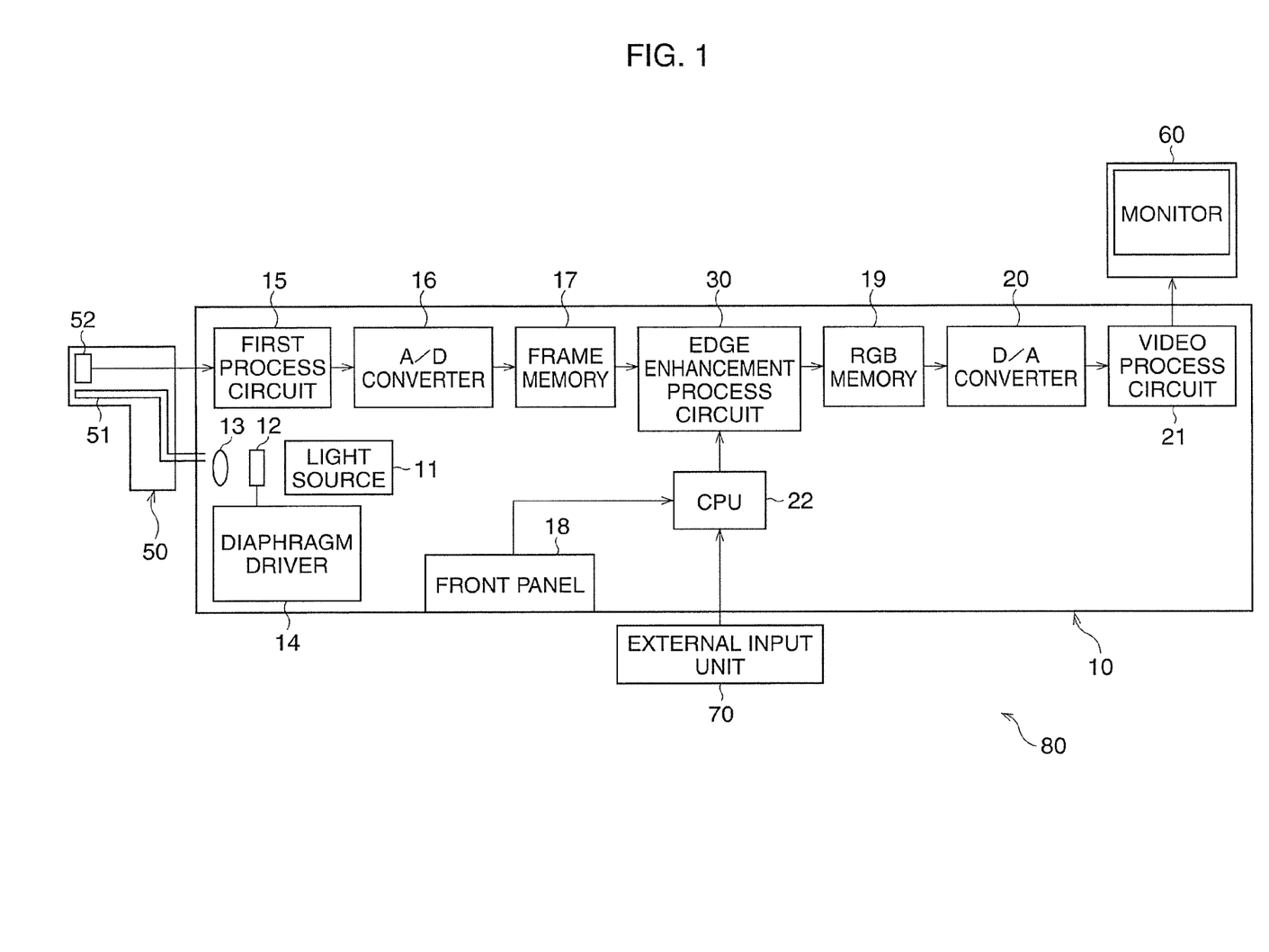
FIG. 1 is a block diagram showing the internal structure of an endoscope processor having an edge enhancement process unit of an embodiment of the present invention.

In FIG. 1, an electronic endoscope system 80 comprises an endoscope processor 10, an endoscope 50, a monitor 60, and other components. The endoscope processor 10 is connected to the endoscope 50 and the monitor 60 via connectors (not depicted).

A light source 11 for illuminating an object (not depicted) is housed in the endoscope processor 10. The light that the light source 11 emits is irradiated to the object via the light guide 51 housed in the endoscope 50.

An optical image of the illuminated object is received by an imaging device 52, such as a CCD, mounted in the endoscope 50. The photographed image is sent as an image signal to the endoscope processor 10. The endoscope processor 10 carries out some predetermined signal processes for the image signals. The image signal, having had the predetermined processes carried out, is sent to the monitor 60. An image, corresponding to the image signal sent to the monitor 60, is displayed on the monitor 60.

The diaphragm 12 and the condenser lens 13 are mounted in the optical path of the light emitted by the light source 11 to the incident end of the light guide 51. The light, which is composed of almost all parallel light beams emitted by the light source 11, is made incident on the incident end, through the condenser lens 13. The condenser lens 13 condenses the light for the incident end.

The intensity of the light made incident on the incident end is adjusted by driving the diaphragm 12. The diaphragm 12 is driven by a diaphragm driver 14.

The light made incident on the incident end is transmitted to an out end (not depicted) by the light guide 51. The transmitted light illuminates a peripheral area near the head end of the insert tube (not depicted). An optical image of the illuminated object is received by the imaging device 52.

A field of an image signal, corresponding to an optical image received by the imaging device 52, is generated by the imaging device 52. The image signal is sent to the first process circuit 15 housed in the endoscope processor 10.

The image signal comprises a plurality of pixel signals generated by a plurality of pixels forming a receiving surface of the imaging device 52. A plurality of pixels is arranged at a receiving surface of the imaging device 52 in a matrix. Each pixel signal is output one by one from the imaging device 52. Pixel signals, generated by pixels arranged in one row, are output one by one from the right end to the left end in one row. After outputting the pixel signals arranged in one row, pixel signals generated by pixels arranged in the next upper row are also output one by one.

The first process circuit 15 carries out the predetermined signal processes; for example, white balance process, color separation process, interpolation process, masking process, and so on, for the image signal. The image signal is separated into RGB signal components by the separation process. Each pixel is covered with one of a red color filter, a green color filter, or a blue color filter. A pixel covered with a red color filter generates only the R signal component in accordance with an amount of received red light component at the pixel. Similarly, a pixel covered with a green color filter generates only the G signal component, and a pixel covered with a blue color filter generates only the B signal component. So, each pixel generates only one of the RGB signal components. The other two color signal components that are not generated by each pixel are interpolated for each pixel by the interpolation process. The side of the image received by the imaging device 52 is colored with black by the masking process. The signal intensity of the RGB signal components for pixels arranged on the side is changed to zero level by the masking process. Incidentally, the signal intensity of RGB signal components corresponding to a pixel not being colored with black is generally higher than zero level.

The image signal, having undergone the signal processing in the first process circuit 15, is then sent to the A/D converter 16. The image signal is converted from an analog signal to a digital signal by the A/D converter 16. The image signal converted to a digital signal is sent to and stored in the frame memory 17. The image signal stored in the frame memory 17 is then sent to the edge enhancement process circuit 30.

The edge enhancement process circuit 30 carries out edge enhancement processing only for pixel signals targeted for edge enhancement, as explained later. The intensity of the edge enhancement is adjusted by the user's input to the front panel 18 or to the external input unit 70.

The image signal, having undergone the edge enhancement processing, is the sent to the RGB memory 19. Next, the RGB signal components of the image signal are separately stored in the RGB memory. The image signal stored in the RGB memory 19 is sent to the D/A converter 20. Subsequently, the image signal is converted from a digital signal to an analog signal by the D/A converter 20.

The image signal converted to an analog signal is encoded by the video process circuit 21. The encoded image signal is sent to the monitor 60. An image of the object is displayed on the monitor 60.

The edge enhancement processing circuit 30 is explained in detail as follows. The signal intensity of a focused pixel, hereinafter referred to as an FP, is enhanced based on eight pixels, hereinafter referred to as SPs, vertically, horizontally, and diagonally surrounding the focused pixel (see FIG. 2) by the edge enhancement process circuit 30. The SP located in the lower right relative to the FP is defined as SP1. The SP located under the FP is defined as SP2. The SP located in the lower left relative to the FP is defined as SP3. The SP located to the right of the FP is defined as SP4. The SP located to the left of the FP is defined as SP5. The SP located in the upper right relative to the FP is defined as SP6. The SP located above the FP is defined as SP7. The SP located in the upper left relative to the FP is defined as SP8.

Figure 3:
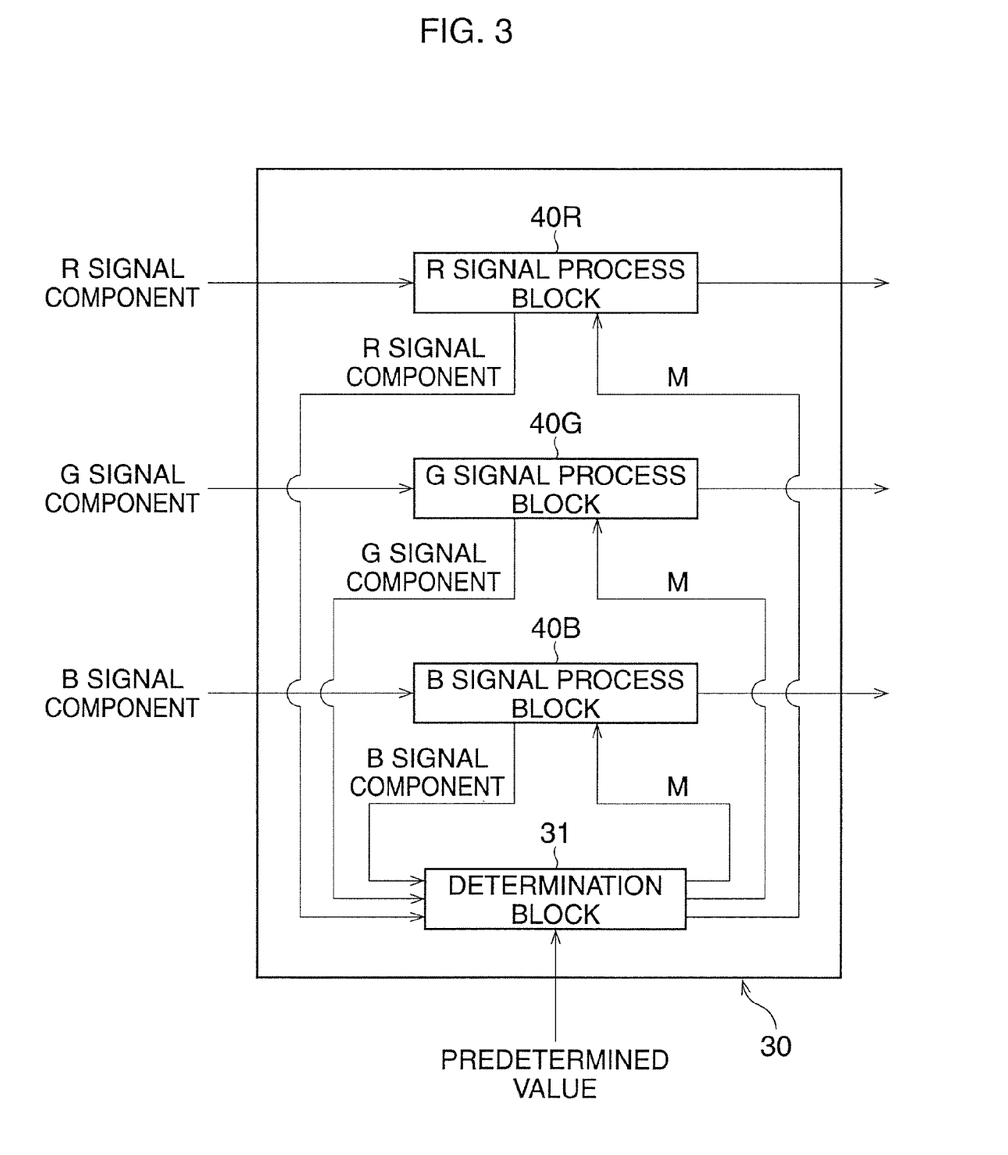
FIG. 3 is a block diagram showing the internal structure of an edge enhancement process circuit.

In FIG. 3, the edge enhancement process circuit 30 comprises an R signal processing block 40R, a G signal processing block 40G, a B signal processing block 40B, and a determination block 31.

The R signal component, the G signal component, and the B signal component output from the frame memory 17 (see FIG. 1) are input to the R signal processing block 40R, the G signal processing block 40G, and the B signal processing block 40B, respectively. As described above, RGB signal components corresponding to each pixel are stored in the frame memory 17. The RGB signal components corresponding to each pixel are input to the RGB signal processing blocks 40R, 40G, and 40B one by one.

The R signal components corresponding to the SPs for one FP are sent from the R signal processing block 40R to the determination block 31. Similarly, the G and B signal components corresponding to the SPs for that FP are sent from the G and B signal processing blocks 40G and 40B to the determination block 31.

Figure 4:
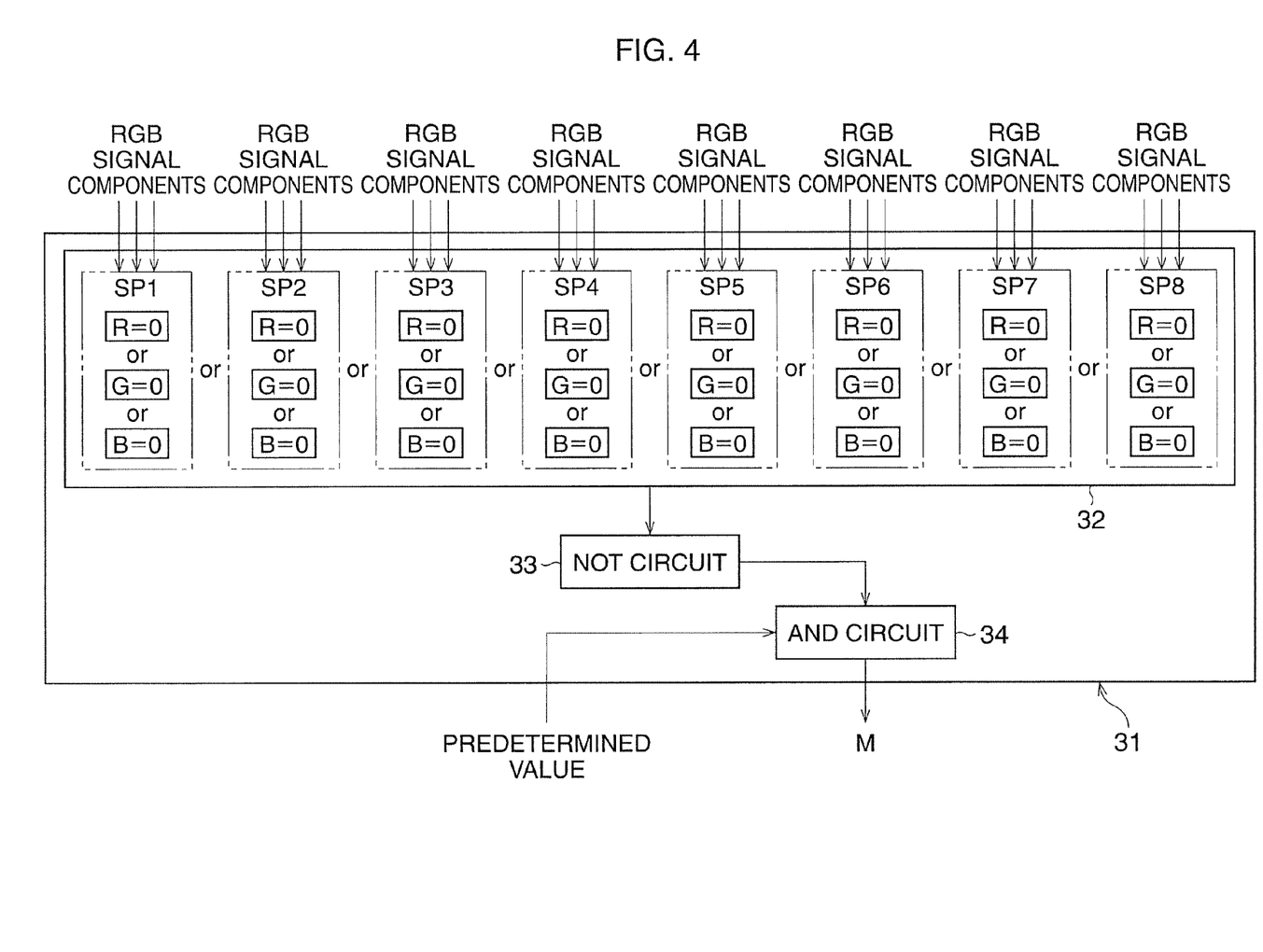
FIG. 4 is a block diagram showing the internal structure of a determination block.

In FIG. 4, the determination block 31 comprises an OR circuit module 32, a NOT circuit 33, and an AND circuit 34.

Figure 2:
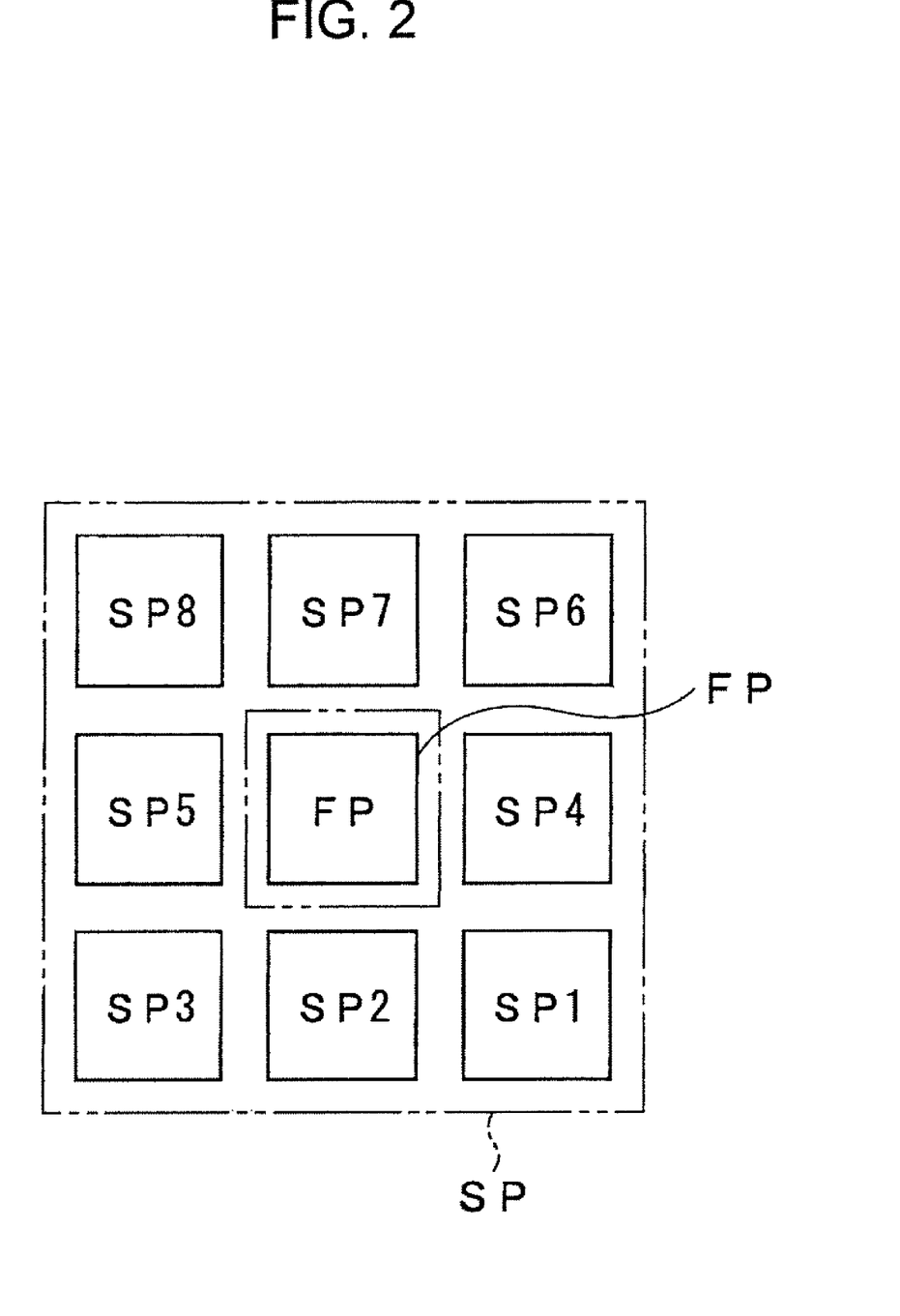
FIG. 2 illustrates the locations of surrounding pixels relative to a focused pixel.

The OR circuit module 32 has eight OR circuits for each of SP1~SP8 (see FIG. 2). The RGB signal components corresponding to SP1~SP8 are input to the OR circuit for SP1~SP8, respectively. When the luminance of one more SP is substantially at zero level, a "one" is output from the OR circuit module 32 to the NOT circuit 33. On the other hand, when the luminances of all SPs are greater than at zero level, a "zero" is output from the OR circuit module 32 to the NOT circuit 33. More concretely, when the signal intensity of one more RGB signal component corresponding to one more SP is substantially at zero level, a "one" is output and sent to the NOT circuit 33. When the signal intensities of all RGB signal components corresponding to all SPs are greater than at zero level, a "zero" is output and sent to the NOT circuit 33.

When a "one" from the OR circuit module 32 is input to the NOT circuit 33, a "zero" is output and sent to the AND circuit 34. On the other hand, when a "zero" from the OR circuit module 32 is input to the NOT circuit 33, a "one" is output and sent to the AND circuit 34.

The AND circuit 34 outputs a coefficient of magnification, hereinafter referred to as M, to the RGB signal processing blocks 40R, 40G, and 40B, according to the signal output from the NOT circuit 33. When a "zero" is output from the NOT circuit 33 to the AND circuit 34, the AND circuit sets the M to be zero, and outputs the set M. On the other hand, when a "one" is output from the NOT circuit 33 to the AND circuit 34, the AND circuit 34 sets the M to be a predetermined value, and outputs the set M. The predetermined value is changed by the CPU 22 according to an input operation of the front panel 18 or the external input unit 70. For example, the predetermined value can be changed to be 0, 2, 4, 6, 8, or 10. An edge in the image is enhanced in proportion to the predetermined value. Further, an edge is not enhanced when the predetermined value is set to be 0.

Figure 5:
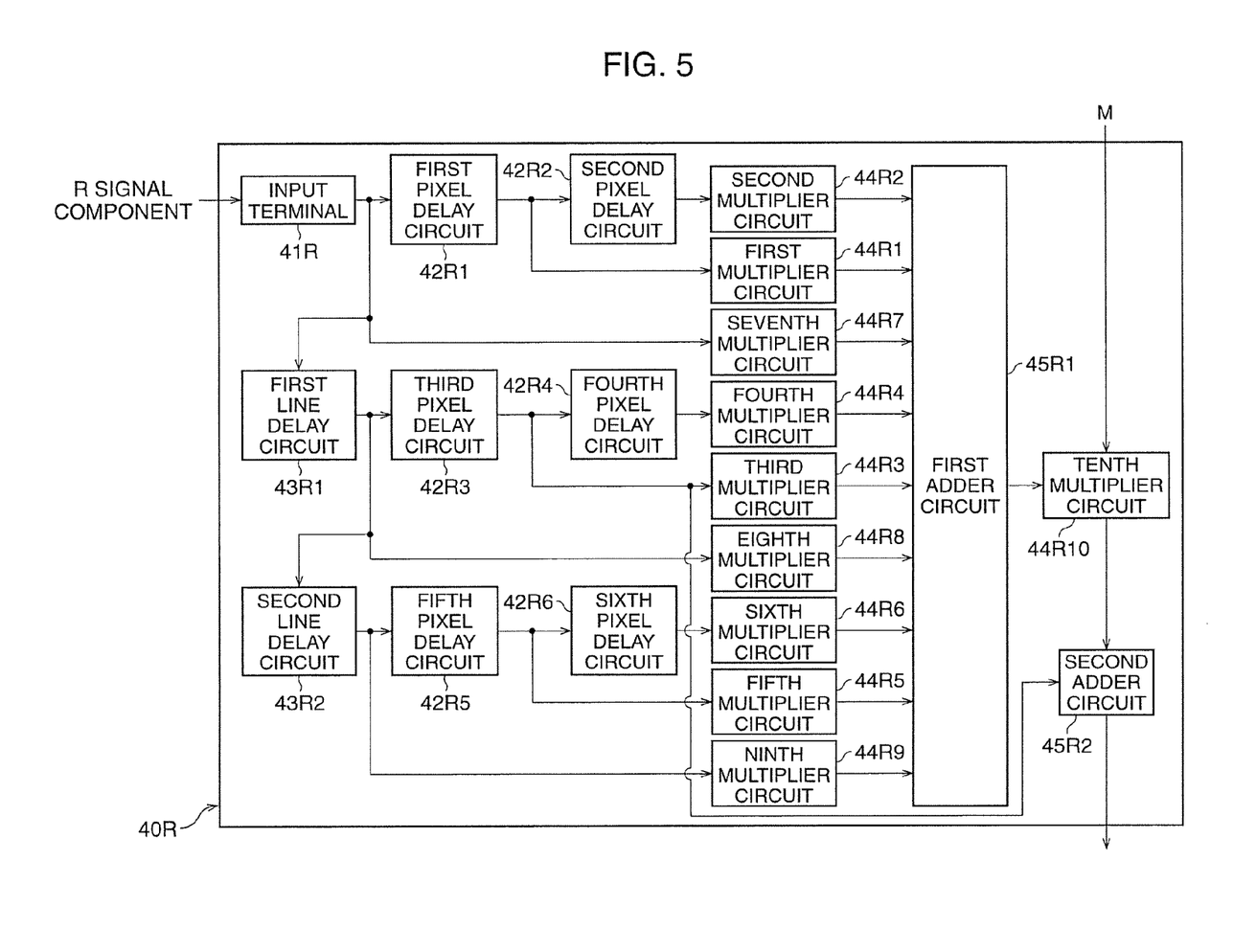
FIG. 5 is a block diagram showing the internal structure of an R signal process block.

Next, an internal structure of the R signal processing block 40R is explained with reference to FIG. 5. The R signal processing block 40R comprises an input terminal 41R, first~sixth pixel delay circuits 42R1~42R6, first and second line delay circuits 43R1 and 43R2, first~tenth multiplier circuits 44R1~44R10, and first and second adder circuits 45R1 and 45R2.

The first~sixth pixel delay circuits 42R1~42R6 delay the output of an input pixel signal for the amount of time that it takes to output one pixel signal. Accordingly, the pixel delay circuits 42R1~42R6 enable the times when the R signal components corresponding to two pixels neighboring each other along a row are output to match each other. The first and second line delay circuits 43R1 and 43R2 delay the output of an input pixel signal for the amount of time that it takes to output one line. Accordingly, the line delay circuits 43R1 and 43R2 enable the times when the R signal components corresponding to two pixels neighboring each other along a column are output to match each other.

The first and second pixel delay circuits 42R1 and 42R2 are connected to the input terminal 41R sequentially. The first line delay circuit 43R1 is connected to the input terminal 41R. The third and fourth pixel delay circuits 42R3 and 42R4 are connected to the output terminal of the first line delay circuit 43R1 sequentially. The second line delay circuit 43R2 is connected to the output terminal of the first line delay circuit 43R1. The fifth and sixth pixel delay circuits 42R5 and 42R6 are connected to the output terminal of the second line delay circuit 43R2 sequentially.

R signal components corresponding to SP1~SP4, FP, and SP5~SP8, hereinafter referred to as RS1~RS4, FRS, and RS5~RS8, respectively are input to the input terminal 41R one by one. When the RS1~RS4, FRS, and RS5~RS8 signal components are input to the input terminal 41R one by one, the RS1, RS2, RS3, RS4, FRS, RS5, RS6, RS7, and RS8 signal components are simultaneously output from the sixth pixel delay circuit 42R6, the fifth pixel delay circuit 42R5, the second line delay circuit 43R2, the fourth pixel delay circuit 42R4, the third pixel delay circuit 42R3, the first line delay circuit 43R1, the second pixel delay circuit 42R2, the first pixel delay circuit 42R1, and the input terminal 41R, respectively.

The R signal components output from the first, second, fourth~sixth pixel delay circuits 42R1, 42R2, 42R4~42R6, the input terminal 41R, and the first and second line delay circuits 43R1 and 43R2 are R signal components, corresponding to the SPs, supposing that the pixel corresponding to the R signal component output from the third pixel delay circuit 42R3 is the FP.

The R signal components output from the first, second, fourth~sixth pixel delay circuits 42R1, 42R2, 42R4~42R6, the input terminal 41R, and the first and second line delay circuits 43R1 and 43R2 are sent to the determination block 31 (see FIG. 3), as described above, and are used for setting M.

The first~sixth multiplier circuits 44R1~44R6 are connected to the output terminals of the first~sixth pixel delay circuits 42R1~42R6, respectively. The seventh multiplier circuit 44R7 is connected to the input terminal 41R. The eighth and ninth multiplier circuits 44R8 and 44R9 are connected to the output terminals of the first and second line delay circuits 43R1 and 43R2, respectively.

The first~ninth multiplier circuits 44R1~44R9 multiply the R signal components, input to the multiplier circuits 44R1~44R9, by predetermined coefficients. The predetermined coefficient for the first, fourth, fifth, and eighth multiplier circuits 44R1, 44R4, 44R5, and 44R8 is −¼. The predetermined coefficient for the second, sixth, seventh, and ninth multiplier circuits 44R2, 44R6, 44R7, and 44R9 is zero. The predetermined coefficient for the third multiplier circuit 44R3 is one.

The R signal components, which are multiplied by the predetermined coefficient, are input to the first adder circuit 45R1. The first adder circuit 45R1 sums up the R signal components input to the first adder circuit 45R1, and then an R signal component of a raw edge-enhancement signal, with the value (FRS−(RS2+RS4+RS5+RS7)/4)), is generated.

The R signal component of the raw edge-enhancement signal is input to the tenth multiplier circuit 44R10. In addition, the M output from the determination block 31 (see FIG. 3) is input to the tenth multiplier circuit 44R10. The tenth multiplier circuit 44R10 multiplies the R signal component of the raw edge-enhancement signal by M, and then an R signal component of the edge-enhancement signal, with the value (M*(FRS−(RS2+RS4+RS5+RS7)/4))), is generated.

The R signal component of the edge-enhancement signal is input to the second adder circuit 45R2. In addition, the FRS, output from the output terminal of the third pixel delay circuit 42R3, is input to the second adder circuit 45R2. The second adder circuit 45R2 adds the FRS to the R signal component of the edge-enhancement signal, and then an edge-enhanced R signal component corresponding to the FP, with the value (FRS+M*(FRS−(RS2+RS4+RS5+RS7)/4))), is generated.

The internal structures of the G and the B signal processing blocks 40G and 40B are the same as that of the R signal processing block 40R. The G and B signal processing blocks generate edge-enhanced G and B signal components corresponding to the FP.

Figure 6:
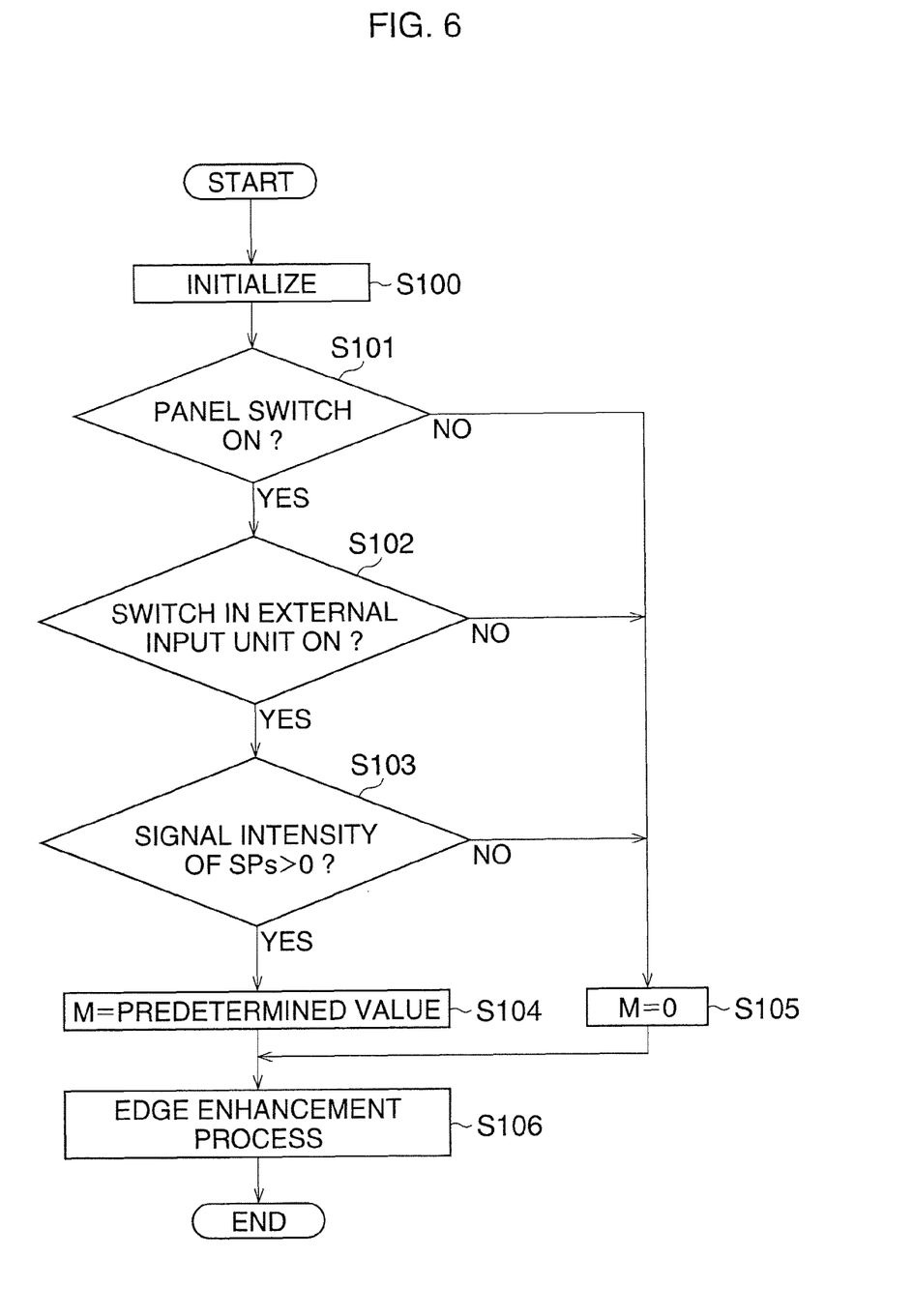
FIG. 6 is a flowchart describing the edge enhancement process carried out by an endoscope processor.

Next, the edge enhancement process carried out by the endoscope processor 10 (see FIG. 1) is explained below using the flowchart of FIG. 6.

The edge enhancement process of this embodiment begins when the image signal is input to the endoscope processor 10, and the signal processes in the first processing circuit 15 are carried out for the image signal.

At step S100, the CPU 22 (see FIG. 1) is initialized. Then, the process proceeds to step S101. At step S101, it is determined whether a panel switch for edge enhancement mounted on the front panel 18 is on or off. If the panel switch is off, the process proceeds to step S105. If the panel switch is kept on, the process proceeds to step S102.

At step S102, it is determined whether a switch for edge enhancement mounted on the external input unit 70 is on or off. If the switch is off, the process proceeds to step S105. If the switch is on, the process proceeds to step S103.

At step S103, it is determined whether the signal intensity of the RGB signal components corresponding to the SPs are greater than zero level. If the signal intensity of one more RGB signal component corresponding to one more SP is at zero level, the process proceeds to step S105. If the signal intensities of all RGB signal components corresponding to all SPs are greater than at zero level, the process proceeds to step S104.

At step S104, M is set to be the predetermined value adjusted according to the input operation of the front panel 18 or the external input unit 70. On the other hand, at step S105, M is set to be zero.

After step S104 or step S105 finishes, the process proceeds to step S106. At step S106, the edge enhancement of the FP is carried out based on the M set at step S104 or step S105. After finishing the edge enhancement of the FP, the edge enhancement process finishes.

Figure 7:
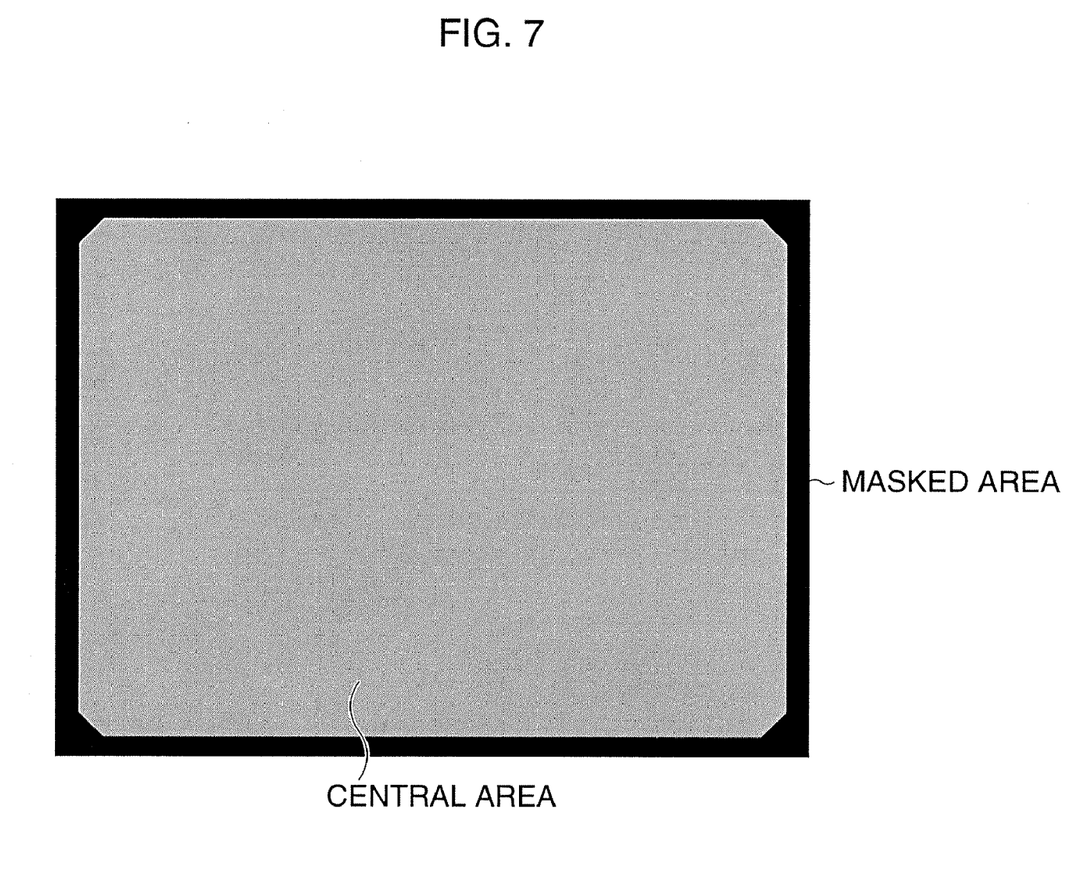
FIG. 7 is an image displayed on a monitor when the edge enhancement process for a pixel neighboring a masked area is stopped.

In the above embodiment, it is able to stop the edge enhancement process for a border between a central area for displaying an object and a masked area colored with black (see FIG. 7). As described above, the side area of an image photographed by the endoscope is often electrically masked with black. However, in the above embodiment, the edge enhancement process for pixels neighboring to the masked area is caused to stop.

Various kinds of endoscopes are connected to an endoscope processor 10 according to one usage. The form of the mask varies according to the connected endoscope. In the above embodiment, the edge enhancement process for pixels neighboring the masked area can be stopped without changing any parts of the circuit in the endoscope processor 10.

The signal intensity of all RGB signal components corresponding to a pixel, excluding an electrically black masked pixel, is ordinarily greater than zero level. In the above embodiment, if the signal intensity of one more RGB signal component corresponding to an SP is at zero level, the determination block then determines that the luminance of the SP is at zero level, and the SP is masked with black. Consequently, even if random noise is mixed with some of RGB signal components corresponding to some of the SPs, the SP can be determined to be masked with black, and the edge enhancement process for the FP can be stopped.

When the FP is a pixel neighboring the masked area, a plurality of SPs are masked with black. However, the luminance level of some SPs that are masked with black may be greater than zero level because of mixed random noise. Therefore, in the above embodiment, to adjust for this problem, the edge enhancement process for the FP is stopped if even one more SP is masked with black. Incidentally, a pixel in the central area never generates a pixel signal that corresponds to complete black. Consequently, the edged enhancement process for a pixel in the central area is unaffected.

It is determined whether an SP is complete black or not based on the signal intensity of the RGB signal components corresponding to the SP in the above embodiment. However, it may be determined whether the luminance of an SP is substantially zero or not. More concretely, it may be determined whether the edge enhancement process for the FP is carried out or not based on the luminance signals corresponding to the SPs.

The edge enhancement process and the determination of whether it is to be carried out for the FP both use the eight pixels arranged in three rows and three columns as SPs around the FP in the above embodiment. However, any pixels arranged in any area around the FP may be used as SPs. For example, even only two pixels vertically or horizontally neighboring to the FP may be used.

The predetermined coefficients for the first~ninth multiplier circuits 44R1~44R9 are decided in the above embodiment. However, any combinations of the predetermined coefficients are adaptable as long as the signal intensity of the RGB signal components corresponding to the FP can be enhanced.

The edge enhancement process is carried out for an image signal output from an endoscope in the above embodiment. However, the same edge enhancement process as the above embodiment may be carried out for an image signal output from an imaging device housed in any apparatus, such as a digital camera.

The above embodiment can be implemented by installing a program for edge enhancement onto an all-purpose endoscope processor. The program for edge enhancement comprises a masking process block code segment, a determination block code segment, and a signal processing block code segment. The masking process block code segment causes a CPU (not depicted) to carry out a masking process for an image signal so that a side of an image is colored in black. The determination block code segment causes a CPU to determine whether the luminance of a surrounding pixel (SP) around a focused pixel (FP) is greater than at zero level. The signal process block code segment causes a CPU to carry out an edge enhancement process for a pixel signal if the luminance of the surrounding pixel (SP) is greater than at zero level.

Although the embodiments of the present invention have been described herein with reference to the accompanying drawings, obviously many modifications and changes may be made by those skilled in this art without departing from the scope of the invention.

The present disclosure relates to subject matter contained in Japanese Patent Application No. 2005-236708 (filed on Aug. 17, 2005), which is expressly incorporated herein, by reference, in its entirety.

The invention claimed is:

1. An edge enhancement processing unit, comprising:
a determination block that determines whether a luminance of a surrounding pixel, which is located around a focused pixel, is greater than at zero level; and
a signal processing block that performs an edge enhancement process for a pixel signal generated by the focused pixel when said determination block determines that said luminance of said surrounding pixel is greater than at zero level;
said signal processing block comprising:
an input terminal that receives a pixel signal generated by a pixel;
first and second pixel delay circuits that are sequentially connected to said input terminal;
first and second multiplier circuits that are connected to output terminals of said first and said second pixel delay circuits, respectively, and that multiply pixel signals, output from said first and said second pixel delay circuits, by first and second coefficients;
a third multiplier circuit that is connected to said input terminal, and that multiplies said pixel signal, output from said input terminal, by a third coefficient;
a first adder circuit that sums said pixel signals output from said first, said second, and said third multiplier circuits;
a fourth multiplier circuit that multiplies said pixel signal output from said first adder circuit by zero when said determination block determines that said luminance of said surrounding pixel is at zero level, and multiplies said pixel signal output from said first adder circuit by a fourth coefficient when said determination block determines that said luminance of said surrounding pixel is greater than at zero level; and
a second adder circuit that adds said pixel signal output from said fourth multiplier circuit to said pixel signal output from said first pixel delay circuit.

2. An edge enhancement processing unit according to claim 1, wherein said determination block determines whether the luminance of said surrounding pixel is greater than at zero level based on said pixel signal output from said input terminal and said second pixel delay circuit.

3. An edge enhancement process unit according to claim 1 comprising:
a determination block that determines whether a luminance of a surrounding pixel, which is located around a focused pixel, is greater than at zero level; and a signal processing block that performs an edge enhancement process for a pixel signal generated by the focused pixel when said determination block determines that said luminance of said surrounding pixel is greater than at zero level;
wherein said signal processing block comprises:
an input terminal that receives a pixel signal generated by a pixel;
first and second pixel delay circuits that are sequentially connected to said input terminal;
a first line delay circuit that is connected to said input terminal;
third and fourth pixel delay circuits that are sequentially connected to said first line delay circuit;
a second line delay circuit that is connected to an output terminal of said first line delay circuit;
fifth and sixth pixel delay circuits that are sequentially connected to said second line delay circuit;
first through sixth multiplier circuits that are connected to each output terminal of said first through said sixth pixel delay circuits, respectively, and that multiply pixel signals, sent output from said first through said sixth pixel delay circuits, by first through sixth coefficients, respectively;
a seventh multiplier circuit that is connected to said input terminal, and that multiplies said pixel signal output from said input terminal by a seventh coefficient;
eighth and ninth multiplier circuits that are connected to each output terminal of said first and said second line delay circuits, respectively, and that multiply said pixel signals output from said first and said second line delay circuits by eighth and ninth coefficients;
a first adder circuit that sums said pixel signals output from said first through said ninth multiplier circuits;
a tenth multiplier circuit that multiplies said pixel signal output from said first adder circuit by zero when said determination block determines that said luminance of said surrounding pixel is at zero level, or that multiplies said pixel signal output from said first adder circuit by a tenth coefficient when said determination block determines that said luminance of said surrounding pixel is greater than at zero level; and
a second adder circuit that adds said pixel signal output from said tenth multiplier circuit to said pixel signal output from said third pixel delay circuit.

4. An edge enhancement processing unit according to claim 3, wherein said determination unit block determines whether the luminance of said surrounding pixel is greater than at zero level based on said pixel signal output from said input terminal and said second line delay circuit.

5. An edge enhancement processing unit according to claim 1, wherein said determination block determines whether the luminance of said surrounding pixel is greater than at zero level by determining whether the signal intensity of a color signal component of the pixel signal corresponding to said surrounding pixel is greater than at zero level.

6. An edge enhancement processing unit according to claim 5, wherein said color signal component is an R signal component, a G signal component, and a B signal component corresponding to the three primary colors of red, green, and blue.

7. An edge enhancement processing unit according to claim 6, wherein said determination block determines that the luminance of said surrounding pixel is greater than at zero level when all signal components of said R signal component, G signal component, and B signal component corresponding to said surrounding pixel are greater than at zero level.

8. An edge enhancement processing unit according to claim 1, wherein said signal processing block carries out an edge enhancement process when the luminance of all of a plurality of said surrounding pixels is greater than at zero level.

9. An edge enhancement processing unit, according to claim 1 comprising:
a determination block that determines whether a luminance of a surrounding pixel, which is located around a focused pixel, is greater than at zero level;
a signal processing block that performs an edge enhancement process for a pixel signal generated by the focused pixel when said determination block determines that said luminance of said surrounding pixel is greater than at zero level;
wherein said signal processing block stops carrying out said edge enhancement process for said pixel signal generated by said focused pixel when said determination block determines that said luminance of said surrounding pixel is at zero level.

10. An edge enhancement processing unit, comprising:
a determination block that determines whether a luminance of a surrounding pixel, which is located around a focused pixel, is greater than at zero level; and
a signal processing block that stops carrying out an edge enhancement process for a pixel signal generated by said focused pixel when said determination block determines that said luminance of said surrounding pixel is at zero level;
wherein said signal processing block comprising:
an input terminal that receives a pixel signal generated by a pixel;
first and second pixel delay circuits that are sequentially connected to said input terminal;
first and second multiplier circuits that are connected to output terminals of said first and said second pixel delay circuits, respectively, and that multiply pixel signals, output from said first and said second pixel delay circuits, by first and second coefficients;
a third multiplier circuit that is connected to said input terminal, and that multiplies said pixel signal, output from said input terminal, by a third coefficient;
a first adder circuit that sums said pixel signals output from said first, said second, and said third multiplier circuits;
a fourth multiplier circuit that multiplies said pixel signal output from said first adder circuit by zero when said determination block determines that said luminance of said surrounding pixel is at zero level, and multiplies said pixel signal output from said first adder circuit by a fourth coefficient when said determination block determines that said luminance of said surrounding pixel is greater than at zero level; and
a second adder circuit that adds said pixel signal output from said fourth multiplier circuit to said pixel signal output from said first pixel delay circuit.

11. An endoscope processor comprising:
a masking process block that performs a masking process for an image signal by receiving an optical image of an object so that a side of an image corresponding to said image signal is black;
a determination block that determines whether a luminance of a surrounding pixel, which is arranged around a focused pixel among pixels forming an image corresponding to said image signal output from said masking process block, is greater than at zero level; and
a signal processing block that performs an edge enhancement process for a pixel signal generated by said focused pixel when said determination block determines that said luminance of said surrounding pixel is greater than at zero level;
wherein said signal processing block comprises:
an input terminal that receives a pixel signal generated by a pixel;
first and second pixel delay circuits that are sequentially connected to said input terminal;
first and second multiplier circuits that are connected to output terminals of said first and said second pixel delay circuits, respectively, and that multiply pixel signals, output from said first and said second pixel delay circuits, by first and second coefficients;
a third multiplier circuit that is connected to said input terminal, and that multiplies said pixel signal, output from said input terminal, by a third coefficient;
a first adder circuit that sums said pixel signals output from said first, said second, and said third multiplier circuits;
a fourth multiplier circuit that multiplies said pixel signal output from said first adder circuit by zero when said determination block determines that said luminance of said surrounding pixel is at zero level, and multiplies said pixel signal output from said first adder circuit by a fourth coefficient when said determination block determines that said luminance of said surrounding pixel is greater than at zero level; and
a second adder circuit that adds said pixel signal output from said fourth multiplier circuit.

12. A computer readable recording medium including a program that causes a computer to execute an edge enhancement process comprising:
performing a masking process for an image signal corresponding to a received optical image of an object so that a side of an image corresponding to said image signal is black;
determining whether a luminance of a surrounding pixel, which is located around a focused pixel among pixels forming an image corresponding to said image signal output from performing of the masking process, is greater than at zero level;
performing an edge enhancement process for a pixel signal generated by the focused pixel if the determining determines that said luminance of said surrounding pixel is greater than at zero level;
wherein the performing of an edge enhancement process comprises:
utilizing an input terminal that receives a pixel signal generated by a pixel;
utilizing first and second pixel delay circuits that are sequentially connected to the input terminal;
utilizing first and second multiplier circuits that are connected to each output terminal of the first and the second pixel delay circuits, respectively, and that multiply pixel signals, output from the first and the second pixel delay circuits, by first and second coefficients;
utilizing a third multiplier circuit that is connected to the input terminal, and that multiplies the pixel signal, output from the input terminal, by a third coefficient;
utilizing a first adder circuit that sums the pixel signals output from the first, the second, and the third multiplier circuits;
utilizing a fourth multiplier circuit that multiplies the pixel signal output from the first adder circuit by zero when the determining determines that the luminance of the surrounding pixel is at zero level, and multiplies the pixel signal output from the first adder circuit by a fourth coefficient when the determination determines that the luminance of the surrounding pixel is greater than at zero level; and
utilizing a second adder circuit that adds the pixel signal output from the fourth multiplier circuit to the pixel signal output from the first pixel delay circuit.

13. An edge enhancement processing unit, comprising:
a determination block that determines whether a luminance of a surrounding pixel, which is located around a focused pixel, is greater than at zero level; and
a signal processing block that stops performing an edge enhancement process for a pixel signal generated by the focused pixel when said determination block determines that said luminance of said surrounding pixel is at zero level;
wherein said signal processing block comprises:
an input terminal that receives a pixel signal generated by a pixel;
first and second pixel delay circuits that are sequentially connected to said input terminal;
a first line delay circuit that is connected to said input terminal;
third and fourth pixel delay circuits that are sequentially connected to said first line delay circuit;
a second line delay circuit that is connected to an output terminal of said first line delay circuit;
fifth and sixth pixel delay circuits that are sequentially connected to said second line delay circuit;
first through sixth multiplier circuits that are connected to each output terminal of said first through said sixth pixel delay circuits, respectively, and that multiply pixel signals, output from said first through said sixth pixel delay circuits, by first through sixth coefficients, respectively;
a seventh multiplier circuit that is connected to said input terminal, and that multiplies said pixel signal output from said input terminal by a seventh coefficient;
eighth and ninth multiplier circuits that are connected to output terminals of said first and said second line delay circuits, respectively, and that multiply said pixel signals output from said first and said second line delay circuits by eighth and ninth coefficients;
a first adder circuit that sums said pixel signals output from said first through said ninth multiplier circuits;
a tenth multiplier circuit that multiplies said pixel signal output from said first adder circuit by zero when said determination block determines that said luminance of said surrounding pixel is at zero level, or that multiplies said pixel signal sent output from said first adder circuit by a tenth coefficient when said determination block determines that said luminance of said surrounding pixel is greater than at zero level; and
a second adder circuit that adds said pixel signal output from said tenth multiplier circuit to said pixel signal sent output from said third pixel delay circuit.

14. An endoscope processor, comprising:
a masking process block that performs a masking process for an image signal by receiving an optical image of an object so that a side of an image corresponding to said image signal is black;
a determination block that determines whether a luminance of a surrounding pixel, which is arranged around a focused pixel among pixels forming an image corresponding to said image signal output from said masking process block, is greater than at zero level; and
a signal processing block that performs an edge enhancement process for a pixel signal generated by said focused pixel when said determination block determines that said luminance of said surrounding pixel is greater than at zero level;

wherein said signal processing block comprises:

an input terminal that receives a pixel signal generated by a pixel;

first and second pixel delay circuits that are sequentially connected to said input terminal;

a first line delay circuit that is connected to said input terminal;

third and fourth pixel delay circuits that are sequentially connected to said first line delay circuit;

a second line delay circuit that is connected to an output terminal of said first line delay circuit;

fifth and sixth pixel delay circuits that are sequentially connected to said second line delay circuit;

first through sixth multiplier circuits that are connected to each output terminal of said first through said sixth pixel delay circuits, respectively, and that multiply pixel signals, output from said first through said sixth pixel delay circuits, by first through sixth coefficients, respectively;

a seventh multiplier circuit that is connected to said input terminal, and that multiplies said pixel signal output from said input terminal by a seventh coefficient;

eighth and ninth multiplier circuits that are connected to output terminals of said first and said second line delay circuits, respectively, and that multiply said pixel signals output from said first and said second line delay circuits by eighth and ninth coefficients;

a first adder circuit that sums said pixel signals output from said first through said ninth multiplier circuits;

a tenth multiplier circuit that multiplies said pixel signal output from said first adder circuit by zero when said determination block determines that said luminance of said surrounding pixel is at zero level, and that multiplies said pixel signal output from said first adder circuit by a tenth coefficient when said determination block determines that said luminance of said surrounding pixel is greater than at zero level; and a second adder circuit that adds said pixel signal output from said tenth multiplier circuit to said pixel signal output from said third pixel delay circuit.

15. An endoscope processor, comprising:

a masking process block that performs a masking process for an image signal by receiving an optical image of an object so that a side of an image corresponding to said image signal is black;

a determination block that determines whether a luminance of a surrounding pixel, which is arranged around a focused pixel among pixels forming an image corresponding to said image signal output from said masking process block, is greater than at zero level; and a signal processing block that performs an edge enhancement process for a pixel signal generated by said focused pixel when said determination block determines that said luminance of said surrounding pixel is greater than at zero level, wherein said signal processing block stops performing said edge enhancement process for said pixel signal generated by said focused pixel when said determination block determines that said luminance of said surrounding pixel is at zero level.

16. A computer readable recording medium including a program that causes a computer to execute an edge enhancement process, comprising:

performing a masking process for an image signal corresponding to a received optical image of an object so that a side of an image corresponding to said image signal is black;

determining whether a luminance of a surrounding pixel, which is located around a focused pixel among pixels forming an image corresponding to the image signal output from the performing of the masking process, is greater than at zero level;

performing an edge enhancement process for a pixel signal generated by the focused pixel when the determining determines that the luminance of the surrounding pixel is greater than at zero level;

wherein performing the edge enhancement process comprises:

utilizing an input terminal that receives a pixel signal generated by a pixel;

utilizing first and second pixel delay circuits that are sequentially connected to the input terminal;

utilizing a first line delay circuit that is connected to the input terminal;

utilizing third and fourth pixel delay circuits that are sequentially connected to the first line delay circuit sequentially;

utilizing a second line delay circuit that is connected to an output terminal of the first line delay circuit;

utilizing fifth and sixth pixel delay circuits that are sequentially connected to the second line delay circuit;

utilizing first through sixth multiplier circuits that are connected to the output terminals of the first through the sixth pixel delay circuits, respectively, and that multiply pixel signals, output from the first through the sixth pixel delay circuits, by first through sixth coefficients, respectively;

utilizing a seventh multiplier circuit that is connected to the input terminal, and that multiplies the pixel signal output from the input terminal by a seventh coefficient;

utilizing eighth and ninth multiplier circuits that are connected to output terminals of the first and the second line delay circuits, respectively, and that multiply the pixel signals output from the first and the second line delay circuits by eighth and ninth coefficients;

utilizing a first adder circuit that sums the pixel signals output from the first through the ninth multiplier circuits;

utilizing a tenth multiplier circuit that multiplies the pixel signal output from the first adder circuit by zero when the determining determines that the luminance of the surrounding pixel is at zero level, and that multiplies said pixel signal output from said first adder circuit by a tenth coefficient when said determination block determines that said luminance of said surrounding pixel is greater than at zero level; and utilizing a second adder circuit that adds the pixel signal output from the tenth multiplier circuit to the pixel signal output from the third pixel delay circuit.

17. A computer readable recording medium including a program that causes a computer to execute an edge enhancement process, comprising:

performing a masking process for an image signal corresponding to a received optical image of an object so that a side of an image corresponding to the image signal is black;

determining whether a luminance of a surrounding pixel, which is located around a focused pixel among pixels forming an image corresponding to the image signal output from the performing of a masking process, is greater than at zero level;

performing an edge enhancement process for a pixel signal generated by the focused pixel when the determining determines that the luminance of the surrounding pixel is greater than at zero level; and wherein the performing of the edge enhancement process for the pixel signal generated by the focused pixel is stopped when the determining determines that the luminance of the surrounding pixel is at zero level.

18. An edge enhancement processing unit according to claim 3, wherein said determination block determines whether the luminance of said surrounding pixel is greater than at zero level by determining whether the signal intensity of a color signal component of the pixel signal corresponding to said surrounding pixel is greater than at zero level.

19. An edge enhancement processing unit according to claim 18, wherein said color signal component is an R signal component, a G signal component, and a B signal component corresponding to the three primary colors of red, green, and blue.

20. An edge enhancement processing unit according to claim 19, wherein said determination block determines that the luminance of said surrounding pixel is greater than at zero level when all signal components of said R signal component, G signal component, and B signal component corresponding to said surrounding pixel are greater than at zero level.

* * * * *